(12) United States Patent
Doerr et al.

(10) Patent No.: US 9,713,653 B2
(45) Date of Patent: Jul. 25, 2017

(54) POLYMER FIBRE

(71) Applicant: MÖLNLYCKE HEALTH CARE AB, Göteborg (SE)

(72) Inventors: Sebastian Doerr, Düsseldorf (DE); Dennis Hansson, Gunnilse (SE)

(73) Assignee: MÖLNLYCKE HEALTH CARE AB, Göteborg (SE)

( * ) Notice: Subject to any disclaimer, the term of this patent is extended or adjusted under 35 U.S.C. 154(b) by 0 days.

(21) Appl. No.: 14/345,363

(22) PCT Filed: Sep. 20, 2012

(86) PCT No.: PCT/EP2012/068537
§ 371 (c)(1),
(2) Date: Mar. 17, 2014

(87) PCT Pub. No.: WO2013/041620
PCT Pub. Date: Mar. 28, 2013

(65) Prior Publication Data
US 2015/0004197 A1    Jan. 1, 2015

Related U.S. Application Data

(60) Provisional application No. 61/536,595, filed on Sep. 20, 2011.

(30) Foreign Application Priority Data

Sep. 20, 2011   (EP) .................................... 11181961

(51) Int. Cl.
| | | |
|---|---|---|
| A61L 15/26 | (2006.01) | |
| A61L 15/22 | (2006.01) | |
| C08G 18/32 | (2006.01) | |
| D01D 5/08 | (2006.01) | |
| D01F 1/10 | (2006.01) | |
| D01F 6/70 | (2006.01) | |
| D01F 6/94 | (2006.01) | |
| C08G 18/48 | (2006.01) | |
| C08G 18/73 | (2006.01) | |
| C08G 18/75 | (2006.01) | |
| C08G 18/76 | (2006.01) | |

(52) U.S. Cl.
CPC ............. *A61L 15/26* (2013.01); *A61L 15/225* (2013.01); *C08G 18/3206* (2013.01); *C08G 18/4808* (2013.01); *C08G 18/73* (2013.01); *C08G 18/758* (2013.01); *C08G 18/7692* (2013.01); *D01D 5/08* (2013.01); *D01F 1/10* (2013.01); *D01F 6/70* (2013.01); *D01F 6/94* (2013.01); *D10B 2331/06* (2013.01); *Y10T 428/298* (2015.01); *Y10T 428/2967* (2015.01)

(58) Field of Classification Search
None
See application file for complete search history.

(56) References Cited

U.S. PATENT DOCUMENTS

| 4,164,603 A * | 8/1979 | Siggel .................... D01D 5/247 264/211 |
| 4,410,694 A | 10/1983 | Nakayama et al. |
| 4,728,323 A * | 3/1988 | Matson ................... A61L 15/46 451/7 |
| 4,847,141 A | 7/1989 | Pazos et al. |
| 5,180,402 A * | 1/1993 | Kubota et al. .................... 8/490 |
| 5,496,909 A * | 3/1996 | Muhlfeld et al. ............... 528/76 |
| 6,017,625 A | 1/2000 | Sato et al. |
| 6,485,665 B1 | 11/2002 | Hermanutz et al. |
| 6,750,163 B2 | 6/2004 | Wang et al. |
| 2002/0106509 A1* | 8/2002 | Figuly et al. ................. 428/364 |
| 2004/0019146 A1* | 1/2004 | Nishikawa ................ D01F 6/94 524/507 |
| 2006/0246798 A1 | 11/2006 | Reneker et al. |

FOREIGN PATENT DOCUMENTS

| EP | 0476756 | | 3/1992 |
| GB | 2203158 | * | 3/1987 |
| JP | 2001214330 | | 8/2001 |
| JP | 2001-526328 A | | 12/2001 |
| JP | 2006-501373 A | | 1/2006 |
| WO | WO-93/12275 | | 6/1993 |
| WO | WO-94/16746 | | 8/1994 |
| WO | WO-03/086234 A2 | | 10/2003 |

OTHER PUBLICATIONS

International Search Report issued Dec. 17, 2012 by the International Searching Authority for PCT Application PCT/EP2012/068537 filed (Inventor—Sebastian Doerr // Applicant—Molnlycke Health Care AB) (4 pages).

* cited by examiner

*Primary Examiner* — Jennifer A Berrios
(74) *Attorney, Agent, or Firm* — Ballard Spahr LLP

(57) ABSTRACT

The present invention provides a polymer fiber comprising a thermoplastic polymer comprising the following building blocks A and B: —O—($CH_2$—$CH_2$—O)n— (A) —O—[$CH_2$]y—O— (B), wherein n is an integer of 10-400, and y is an integer in the range of 2 to 16, wherein A is present in an amount of 15-30 mole %, B is present in an amount of 20-40 mole % and wherein building blocks A and B are linked by the following linking group C: —[(C=O)—NH—$CH_2$—$CH_2$—$CH_2$—$CH_2$—$CH_2$—$CH_2$—NH—(C=O)]— (C) wherein C is present in an amount of 45-55 mole %. The present invention further relates to a method for preparing a polymer fiber, absorbent articles comprising a polymer fiber and the use of a fiber in a product for treating wounds and/or burns.

24 Claims, No Drawings

POLYMER FIBRE

CROSS-REFERENCE TO RELATED APPLICATIONS

The present application is a U.S. National Phase Application of International Application No. PCT/EP2012/068537, filed Sep. 20, 2012, which International Application claims priority to European Patent Application No. 11181961.1, filed Sep. 20, 2011, and U.S. Provisional Application No. 61/536,595, filed Sep. 20, 2011, all of which applications are incorporated herein fully by this reference.

TECHNICAL FIELD OF THE INVENTION

The present invention relates to polymer fibres displaying suitable properties for use in inter alia absorbent products, for instance wound dressings.

BACKGROUND ART

Polymers with super-absorbing capacity are frequently used within various technical fields and for various applications. Some of the most common super-absorbents are polyacrylic acid sodium salts and carboxymethyl cellulose (CMC) sodium salts. These are frequently used in absorbing materials in the form of powders, and often in combination with cellulose fibres, etc. For many applications it is beneficial to have the super-absorbent polymer in another form than powder, since powder has a tendency to migrate and escape, thereby generating dust. Another problem with super-absorbents in powder form is gel blocking. Gel blocking means that the powder agglomerates and when the agglomerate comes in contact with polar liquid a gel layer is formed on the surface of the agglomerate. The gel layer on the surface of the agglomerate prevents the liquid from reaching the super-absorbents in the center of the agglomerate. One way to overcome the problems associated with super-absorbing powder is to form fibres from the polymer. Fibres of polyacrylic acid sodium salt can be made by dry spinning of low molecular weight polymer and subsequent cross-linking of the dried fibre. The absorbency and thickening, gelling effect in polar liquid tend to be lower for those fibres compared to the powder form, as a result of insufficient cross-linking. In various applications, like wound fillers, there is a reluctance to use polyacrylic acid sodium salts due to the risk of allergic reactions caused by residual monomers and by-products from for instance the initiators.

Absorbing materials based on sodium calcium alginate and/or sodium CMC constitute archetypical polymeric materials within wound care. Fibres of sodium calcium alginate can be formed by wet spinning of a solution (dope) of sodium alginate that is pumped into a coagulation bath via small orifices (a spinneret). In the coagulation bath an ion exchange between calcium ions and sodium ions take place and "alginate fibres" are formed. A drawback with this process is that it is difficult to make soluble fibres since the calcium ion forms a cross-link between the molecules that hardly can be reversed unless complexing agents are used. The process used to form alginate fibres is described in EP 476 756. Other drawbacks of the wet spinning process are that it is slow and requires several steps of drying, etc.

Fibres that dissolve and gel are useful in order to maximize liquid absorption. Fibres which do not dissolve absorb a certain amount of liquid but residual liquid may remain outside the fibres. When fibres dissolve they will form a hydrogel, which exhibit advantages relating to absorption of larger amounts of liquid in the gel. To overcome the disadvantage of non-dissolving fibres, such as alginate fibre, fibres based on CMC was developed. CMC is not thermoplastic so the production has to be performed by modification of cellulose fibres. In the case of Aquacel (a commercial product from ConvaTec) a regenerated cellulose fibre such as Lyocell is used as starting material. The cellulose fibre is processed chemically to form a sodium CMC fibre, as disclosed in U.S. Pat. No. 4,410,694, WO 93/12275 and WO 94/16746. A disadvantage pertaining to this procedure is the inflexibility of the process and the sensitivity of the ionic groups in the polymer against dibasic cations such as calcium ions, which are often present in body fluids.

In practice it is often beneficial to balance the solubility of the fibres so that it is just on the border between full dissolution and not being dissolved. This can be achieved either by physical or chemical cross-linking between the polymer strands. If the number of cross-links is too high it will lead to a fibre with poor absorption capacity. If on the other hand the number of cross-links is too low this can lead to a weak gel, depending on the type, concentration and molecular weight of the polymer. By chemical cross-linking is meant a covalent bond between two or more polymer strands. Physical cross-linking can be achieved by crystalline parts, hydrogen bonding, ionic groups that interact or by hydrophobic interactions. A combination of the previously mentioned interactions is also possible.

In U.S. Pat. No. 6,750,163 a way of making melt processable polyethylene oxide fibres is described. The purpose of these fibres is to be easily dissolvable but they cannot be used to form strong gels at low concentrations.

Further, U.S. Pat. No. 6,017,625 discloses a method of making water-absorptive polyurethane fibres. Explicit examples show fibres prepared by using MDI methylene bis(p-phenyl isocyanate) (MDI) together with polyethylene glycol (PEG).

SUMMARY OF THE INVENTION

There is consequently a substantial need in the art for providing fibres that are amenable for facile and inexpensive preparation and that possess improved properties pertaining to aspects such as dissolution and gelling, in order to enable the formation of hydrogels with high absorbency and high specific strength.

The above-mentioned objects as well as other objects of the invention, which can be gathered by a person skilled in the art after having studied the description below, are met by the different aspects of the disclosed invention.

The present invention fulfils the above-identified needs, as it provides, inter alia, polymer fibres displaying desirable properties in terms of inter alia absorbency, strength, gelling, and dissolution, as well as processes and methods for preparing the polymer fibres, and various products and uses employing the fibres in question.

As a first aspect of the invention, there is provided a polymer fibre comprising a thermoplastic polymer comprising the following building blocks A and B:

n indicating a repeating unit and being an integer of 10-400, and y being an integer in the range of 2 to 16, wherein:

A is present in an amount of 15-30 mole %,

B is present in an amount of 20-40 mole %,
wherein building blocks A and B are linked by the following linking group C:

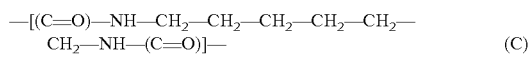
(C)

wherein
C is present in an amount of 45-55 mole %.

As a second aspect of the invention, there is provided a polymer fibre obtainable from a thermoplastic polymer, wherein the thermoplastic polymer is obtained by reacting a group of components comprising hexamethyl diisocyanate (HDI); at least one polyol; and at least one chain extender wherein the at least one chain extender comprises a diol and wherein the molar ratio of polyol to chain extender is from 20:80 to 65:35.

In a third aspect the present invention relates to a process for the preparation of polymer fibres, comprising, inter alia, the steps of providing a suitable polymer, melting it, and subsequently preparing polymer fibres from the melted polymer.

In a fourth aspect, the present invention relates to absorbent articles, such as for instance wound dressings, ostomy devices, diapers, sanitary napkins, panty liners or the like, wherein the articles comprise polymer fibres in accordance with the present invention. In a fifth aspect, the present invention pertains to the use of the polymer fibres as per the present invention, for instance in products for treating and/or protecting wounds and/or burns.

Thus, the present invention provides polymer fibres that can be produced in a facile, highly scalable and inexpensive manner, and that possess highly desirable properties relating to inter alia absorbency, specific strength, gelling, and dissolution.

DETAILED DESCRIPTION OF THE INVENTION

The present invention pertains to, inter alia, polymer fibres obtainable by melt spinning and/or by non-woven melt processes, having desirable properties in terms of, inter alia, absorbency, as well as processes for preparing the polymer fibres. Further, the present invention additionally relates to products comprising the polymer fibres, as well as uses of the polymer fibres for various purposes and applications.

Where features, embodiments, or aspects of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. Additionally, it should be noted that embodiments and features described in the context of one of the aspects and/or embodiments of the present invention also apply mutatis mutandis to all the other aspects and/or embodiments of the invention. For example, the at least one chain extender described in connection with the aspects/embodiments relating to the polymer fibres may naturally also apply mutatis mutandis in the context of the processes and/or the articles of the present invention, and naturally vice versa, and, further, for instance, all details mentioned in connection with the polymer fibre and/or the processes relate to all other embodiments and/or aspects and also concern e.g. embodiments in the form of core-sheath, island-in-a-sea, and/or side-by-side, all in accordance with the present invention as such.

As a first aspect of the invention, there is provided a polymer fibre comprising a thermoplastic polymer comprising the following building blocks A and B:

(A)

(B)

n indicating a repeating unit and being an integer of 10-400, and
y being an integer in the range of 2 to 16,
wherein:
A is present in an amount of 15-30 mole %,
B is present in an amount of 20-40 mole %,
wherein building blocks A and B are linked by the following linking group C:

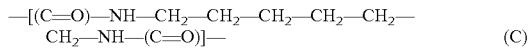
(C)

wherein
C is present in an amount of 45-55 mole %.

The term "thermoplastic polymer" refers to a polymer that may be moldable above a specific temperature but is able to return to a solid state as the temperature decreases, i.e. upon cooling of the polymer. The thermoplastic polymer may comprise both straight and branched sections.

The building blocks of the thermoplastic polymer and the linking group may thus be linked as

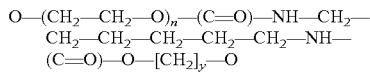

As an example, n may be between 90-250.

The first aspect of the invention is based on the insight that a polymer comprising building blocks A and B with C as linking group has a high melting point, which facilitates the preparation of a fibre from the thermoplastic polymer. In addition, such a fibre exhibits superior absorption capacity, as seen in the Examples below. Further, the specific molar ranges of the building blocks and linking group facilitate the formation of a thin fibre. The present invention is further based on the surprising insight that a polymer that comprises such a large mole % of building block A, which gives rise to a high absorption capacity, may also have a high melting point if A is used together with building blocks B and with C as linking group in the specified molar ranges. This is further seen in the experimental examples below.

The mole % may be the mole % of the entire thermoplastic polymer or it may indicate the ratio between A, B and C. The mole % of A, B and C may sum up to 100%. The thermoplastic polymer may however comprise additional components.

In embodiments of the first aspect, the molar ratio of building block A to building block B is from 20:80 to 65:35, such as from 35:65 to 50:50. Further, in embodiments of the first aspect, the molar ratio of building block A to linking group C is from 20:80 to 50:60, such as from 25:75 to 35:65. Moreover, in embodiments of the first aspect, the molar ratio of building block B to linking group C is from 30:70 to 45:55, such as from 35:65 to 40:60.

Further, the molar ratio between A, B and C may be A:B:C=(15-30:20-40:45-55).

Further, the fibres according to the present invention are more flexible in terms of processability compared to for instance carboxymethyl cellulose fibres. The present invention overcomes the problems associated with existing products and/or technologies, as the invention relates to a fibre that can be processed in existing process equipment for melt spinning and/or nonwoven making. Fibre-forming polymers must possess adequate properties in terms of: (1) length (molecular weight), (2) melt viscosity, (3) a high degree of intramolecular and intermolecular attraction, whether through primary chemical bonds or other attractive forces, (4) the ability to be oriented along the axis of the fibre; (5) the ability to form well-ordered crystals or pseudocrystals, (6) moieties with two different Tg, one higher than room temperature and one lower, is beneficial, (7) the right balance between crystalline and amorphous regions. There are not many thermoplastic polymers which fulfill these features, and only certain polymers can be meltspun. Thus, it is a surprise to find that the polymers according to the present invention enables melt spinning of polymer fibres, and at the same time it is a polymer that forms strong hydrogels with for instance polar liquids, such as for instance wound fluids and/or any other types of body fluids.

The present invention thus relates, inter alia, to a new polymer fibre spun from a thermoplastic polymer. The polymer fibres swell and/or dissolve in and/or absorb liquids, for instance water and/or wound fluid and/or body fluids, and form a strong gel. The fibres are made of polymers that are physically or non-covalently cross-linked in a thermo reversible supramolecular manner. Various types of inter-chain interactions endow the polymer fibre with strong gelling properties. Further, the composition of the polymer enables melt spinning the fibres, or to produce fibres in nonwoven melt processes. Further, the hydrophilic nature of the polymer makes it possible for the polymer to dissolve and gel and the polymer fibre will produce a strong hydrogel, when the fibre absorbs polar liquids. Moreover, the polymer fibres can form strong gels at low concentrations, a crucial feature when utilized in absorbent products, for instance wound dressings. Additionally, it may be important to have a wet surface of fibres against for example a wound, which is the case for the polymer fibres according to the present invention, which are gelled when absorbing liquid.

The polymer fibre may also swell and absorb its own weight several-fold. This property may be an advantage if the fibres are used in a wound dressing, in which the fibres according to the present invention may be mixed with some other kind of fibres, such as cellulose fibres and/or polyester fibres in a wound dressing or an absorbent article. A fibre that swells, but that does not dissolve, may provide advantages in terms of, inter alia, preserved integrity, which may be beneficial for certain applications.

As further stated above, the polymer fibres in accordance with the present invention have improved absorbency, since the polymer used in the present invention is less sensitive to dibasic cations, such as calcium ions, which are often present in body fluids. Further, the flexible interactions between the polymer chains enable reformulation, with the implication that gel forming is reversible. This can be an advantage in, for instance, a wound, where pockets of wound fluids can form if the gel is not filling the voids completely. Further, the handling is easier when using a thermoplastic polymer compared to for example CMC fibres. Carboxymethyl cellulose fibres are made in a more complicated process, as disclosed in the background of the present invention. The fibres according to the present invention may, in contrast, be produced in a facile manner from granules of the polymer which may be stored for extended periods of time.

Building block B may for example originate from a chain extender, such as a diol.

In embodiments of the first aspect, linking group C originates from hexamethyl diisocyanate (HDI).

Thus, the thermoplastic polymer may be a polyurethane polymer.

The inventors have found that the presence of HDI facilitates a high "packing ratio" of hard segments of the polymer, such as B-C segments of the polymer. The HDI gives rise to urethane linkages. However, it is further to be understood that HDI may be hydrolyzed and then give rise to urea linkages and thus, as would be appreciated by the skilled person, the polymer fibre may also comprise urea linkages.

In other words the present inventors have shown that the use of HDI results in a thermoplastic polymer with a higher melting point which makes melt spinning easier and improves the properties of the obtained fibre. The higher melting point makes the fibre easier to sterilize and to treat further.

In embodiments of the first aspect, the thermoplastic polymer further comprises building blocks that originate from other diisocyanate compounds than HDI.

The other diisocyanate compounds may be selected from for instance be selected from the group comprising methylene bis(p-phenyl isocyanate) (MDI), toluene diisocyanate (TDI), isophorone diisocyanate (IPDI), 1,5-naphtalene diisocyanate, 1,6-hexamethylene diisocyanate (HDI), paraphenylene diisocyanate (PPDI), 1,4 cyclohexane diisocyanat (CHDI), tetramethylxylenediisocyanate (TMXDI), 3,3-bitoluene diisocyanate (TODI), and methylene bis(p-cyclohexyl isocyanate) (HMDI), and any combination thereof.

It is to be understood that the thermoplastic polymer may comprise further building blocks in addition to A, B, and C above. As an example, the thermoplastic polymer may further comprise at least one polymer selected from the group comprising polyurethanes, polyethers, polyesters, and polyamides, depending on the desired properties of the fibre and of the subsequent products. In a preferred embodiment, the at least one further polymer is a polyurethane. In another embodiment, the polymer fibre may comprise a polyurethane polymer that comprises, inter alia, polyethylene glycol (PEG), polyethers, polyesters, co-polymers of polyethers and polyesters, co-polymers comprising PEG, as well as any other hydrocarbon polymers substituted with heteroatoms, preferably oxygen and/or nitrogen and/or silicon atoms, in order to endow the polymer and the polymer fibre with suitable properties. Further, groups that can form anionic and/or cationic moieties in water or other polar fluids, such as carboxylic acids and/or sulphonic acids and/or amines, etc., can also be copolymerized into the polymer.

As a configuration of the first aspect, the thermoplastic polymer of the polymer fibre may comprise hexamethyl diisocyanate (HDI) reacted with at least one polyol and at least one chain extender, wherein the at least one chain extender comprises a diol and wherein the molar ratio of polyol to chain extender is from 20:80 to 65:35. The polyol may be polyethylene glycol (PEG).

The molar ratio of polyol to chain extender may from 35:65 to 50:50. Fibres having a molar ratio of polyol to chain extender from 35:65 to 50:50 has been found to have exceptional high melt temperature in combination with a large absorption capacity, as seen in the experimental examples below.

In embodiments of the first aspect of the invention, building block A may originate from polyethylene glycol (PEG).

PEG is a polymer that gives the fibre a high absorption capacity. In accordance with one embodiment, when the polymer fibre comprises PEG as the main polymer component, PEG may have an average molecular weight between 2000 and 8 000 Da. At lower molecular weights, the solubility and/or ability to absorb water and other (polar) liquids decrease, whereas at higher molecular weight the processability in melt spinning equipment decreases. The gel strength in water peaks at a PEG molecular weight between 3000 and 8000 Da. These properties may however be altered depending on the remaining components of the polymer, for instance chain extenders and diisocyanates, meaning that PEG may have essentially any molecular weight, for instance between 400 Da and 50 kDa. Different average molecular weight of the PEG can be achieved by changing to a grade with higher or lower molecular weight, but it can also be achieved by mixing grades of different molecular weight.

As an example, the PEG may comprise two isocyanate reactive groups.

As an example, the thermoplastic polymer fibre may comprise inter alia between approximately 70-95 weight % polyethylene glycol, for example between approximately 81-94 weight % polyethylene glycol, for example between approximately 84-93 weight % polyethylene glycol.

As an example, the number average molecular weight of the PEG may be between 400-16000 g/mol, such as between 1000-10000 g/mol, such as between 2000-8000 g/mol, such as between 4000-10000 g/mol.

The number average molecular weight is well known to the skilled person. The number average molecular weight of a polymer is the arithmetic mean or average of the molecular weights of the individual macromolecules.

PEG having a number average molecular weight between 400-16000 g/mol, such as between 1000-10000 g/mol, such as between 2000-8000 g/mol, such as between 4000-10000 g/mol has been found to have excellent properties, as seen in the experimental examples below.

Furthermore, building block A may originate from a first polyethylene glycol polymer (PEG) and a second polyethylene glycol polymer (PEG), wherein the number average molecular weight of the first PEG is different than the number average molecular weight of the second PEG.

As an example, the first polyethylene glycol polymer (PEG) may have a number average molecular weight of 400 to 3,000 g/mol and the second first polyethylene glycol polymer (PEG) may have a number average molecular weight of 6,000 to 16,000 g/mol.

As a further example, the molecular weight of the first polyethylene glycol is from 1,000 to 2,000 g/mol and the molecular weight of the second polyethylene glycol is from 6,000 to 9,000 g/mol.

Furthermore, the first PEG may have a number average molecular weight of 400 to 4000 g/mol, such as 400 g/mol or more, or 700 g/mol or more, or 1,000 g/mol or more, or 1,500 g/mol or more; or 4,000 g/mol or less, or 3,500 g/mol or less, or 3,000 g/mol or less or 2,500 g/mol or less. The second PEG may have a number average molecular weight of 5,000 to 20,000 g/mol, such as 5,000 g/mol or more, 6,000 g/mol or more, or 7,000 g/mol or more, or 8,000 g/mol or more, or 20,000 g/mol or less, or 18,000 g/mol or less or 16,000 g/mol or less, or 14,000 g/mol or less, or 12,000/mol or less, or 9,000 g/mol or less.

The inventors have found that if the thermoplastic polymer has been prepared using a mixture of two PEGs facilitates the preparation of a fibre having increased absorption capacity, as seen in the experimental section.

Furthermore, a thermoplastic polymer comprising two, or more than one PEG, facilitates preparation of thinner fibres, as seen in the experimental examples below.

Without being bound by any theory, it is believed that a PEG having a high number average molecular weight, e.g. the second PEG, may result in a high absorption capacity since it gives rise to long hydrophilic "blocks" on the thermoplastic polymer. Further, a PEG having a lower number average molecular weight, e.g. the first PEG, may in addition give the polymer extra strength due to the formation of further urethane linkages. Thus, combining two such PEGs within the same polymer, the formed polymer may get both of the such properties. Further, the inventors have shown that the melting point is more or less not affected by mixing two PEGs. In other words, it may be advantageous to use two PEGs of different number average molecular weights since it facilitates incorporation of further blocks originating from HDI, which gives the prepared polymer a high melting point, but still have a large amount of PEG in the prepared polymer, which gives the polymer a high absorption capacity. Thus, the prepared polymer is easy to use in e.g. melt spinning processes but retains a high absorption capacity.

As an example, the molar ratio between the first and the second polyethylene glycol is from 1:1 to 1:10, such as 1:2 to 1:6.

As an example the molar ratio between the first and the second polyethylene glycol may be from 1:1 to 1:10, such as 1:1 or more, or 1:2 or more, or 1:3 or more, or 1:4 or more, or 1:10 or less, or 1:8 or less, or 1:6 or less, or 1:5 or less; for example 1:2 to 1:6. The molar ratio is calculated according to:

$$n_{PEG1}/n_{PEG2}$$

wherein $n_{PEG1}$ denotes the number of moles of the first PEG and $n_{PEG2}$ denotes the number of moles the second PEG.

In embodiments of the first aspect of the invention, the thermoplastic polymer has a melting point of at least 70° C., such as at least 80° C. such as at least 100° C.

As discussed above, a thermoplastic polymer having a melting point of above 70° C. facilitates use and handling during e.g. melt spinning. It is believed that the molar percent of linking group C gives the thermoplastic polymer a high melting point.

In embodiments of the first aspect, the thermoplastic polymer is substantially linear.

In other words, the polymer constituting the polymer fibre may be substantially linear, that is the branching of the polymer is reduced as much as possible.

A substantially linear polymer is advantageous in that it facilitates preparation of a polymer fibre of higher strength.

A substantially linear polymer may be prepared by using specific catalysts and/or stabilizers when preparing the polymer. Such a catalyst may for example be dibutylphosphate and/or tin-II-ethylhexanoate. A substantially linear or straight polymer may also be prepared by reacting the components forming the polymer at a first temperature and then rising the temperature to a second higher temperature, as seen in the Examples of the present invention.

The thermoplastic polymer may further be described as a polymer having hard and soft segments, wherein the soft segments gives the polymer a high absorption capacity and the hard segments gives the polymer a high melting point.

Consequently, the thermoplastic polymer may comprise soft and hard segments and wherein the hard segments comprises B and C building blocks and the soft segments comprises A building blocks.

In embodiments of the first aspect, building block B originates from at least one diol.

The at least one diol may be selected from the group comprising 1,4 butanediol, 1,6-hexanediol, 1,8-octanediol, 1,10-decanediol, 1,12-dodecanediol, cyclododecanediol, 1,14-tetradecanediol, 1,16-hexadecanediol.

As an example, the at least one diol may be 1,4 butanediol.

The inventors have found that the combination of HDI (for component C) and 1,4 butanediol (for component B) gives a high packing ratio of "hard segments" in the polymer, which thus gives the polymer a high melting point and further facilitates a large amount of soft segments, such as PEG, thereby giving the polymer a high absorption capacity. HDI and 1,4 butanediol may further give rise to a structure that is easily crystallised and gives a good phase separation As a second aspect of the invention, there is provided a polymer fibre obtainable from a thermoplastic polymer, wherein the thermoplastic polymer is obtained by reacting a group of components comprising
  hexamethyl diisocyanate (HDI);
  at least one polyol; and
  at least one chain extender
    wherein the at least one chain extender comprises a diol and wherein the molar ratio of polyol to chain extender is from 20:80 to 65:35

The terms and definitions used in relation to the second aspect are as defined in relation to the first aspect above.

In embodiments of the second aspect, the at least one polyol is selected from at least one polyether and/or polyester.

In embodiments of the second aspect, the at least one polyol is a PEG as described in relation to the first aspect above.

In embodiments of the second aspect, the diol is as described in relation to the first aspect above Furthermore, the thermoplastic polymer may be as described in relation to the first aspect above The second aspect of the invention is based on the insight that a polymer according to the first aspect may be prepared by reacting HDI with a polyol and a diol as a chain extender. In other words, HDI may form linking group C in the reacted thermoplastic polymer, a PEG may form building block A and a diol may form building block B.

Reacting the components may for example comprise heating, such as heating above a specific temperature.

In embodiments of the second aspect, the molar ratio of polyol to chain extender may from 35:65 to 50:50.

In embodiments of the second aspect, the fibre is obtainable by melt spinning.

As will be apparent from the description and the examples, the term "melt spinning" shall be understood to relate to the process where a thermoplastic polymer is molten and formed to fibres, the term "non-woven melt processes" shall be understood to pertain to meltblowing and/or spunlaying processes, but other processes and methods are naturally within the scope of the present invention.

To be considered spinnable the polymer has to be capable of being melt drawn to a draw ratio of at least 6 times (i.e. a draw ratio of at least 6), where the draw ratio is defined as the orifice diameter in the spinneret divided with the fibre diameter after hot stretch but before cold stretch. The fibre must also have sufficient strength and it should not be too tacky so that the fibres stick together.

The lab set up for testing fibre spinning was carried out as follows: A KFM Eco Ex 18 extruder with a screw size of 18×520 mm and mixing zones was used to extrude the polymer through a spinneret. The orifice in the spinneret was 0.5 mm and spinnerets with between 2 and 24 holes were used. The extruder was equipped with 7 heating zones and a water cooled inlet. The speed of the extruder was set so that the residence time for the polymer in the extruder was approximately 10 minutes. The temperature setting in the extruder varied with polymer and was typically 85° C. in zone 1 to 3 and between 120° C. and 210° C. in zone 4-7. The fibres were collected on a winder with a maximum peripheral speed of 515 m/min. The distance between the spinneret and the winder was varied between 0.5 meters to 3 meters.

In a configuration of the second aspect, the polymer fibre is obtainable by melt spinning a thermoplastic polymer, wherein the thermoplastic polymer is obtained by reacting at least the following components:
  a. at least one diisocyanate compound wherein at least one is hexamethyl diisocyanate;
  b. at least one chain extender having two isocyanate reactive groups wherein the isocyanate reactive groups are hydroxyl groups and/or amine groups;
  c. a first polyethylene glycol polymer having a number average molecular weight of 400 to 3,000 g/mol;
  d. a second polyethylene glycol polymer having a number average molecular weight of 6,000 to 16,000 g/mol; and
  e. optionally any polymer comprising at least two isocyanate reactive groups;

As an example, each of the first and the second polyethylene glycol polymer comprises two isocyanate reactive groups wherein the isocyanate reactive groups are hydroxyl groups and/or amine groups.

Further, the total number average molecular weight of the thermoplastic polymer may be at least 10,000 g/mol but not more than 1,000,000 g/mol.

The molar ratio between the at least one diisocyanate compounds and the sum of the first and the second polyethylene glycol may be from 1.0:1.0 to 10.0:1.0.

The molar ratio between the number of isocyanate groups of the at least one diisocyanate compound and the sum of all isocyanate reactive groups of the chain extender and the first and the second polyethylene glycol and the optionally any polymer comprising at least two isocyanate reactive groups may be between 0.90 to 1.1.

The polymer fibres of the present invention may be remarkably thin. This is seen by the low dtex values of the prepared polymers in the Experimental examples. Dtex is the mass in grams per 10,000 meters of fibre, i.e. a known unit for the linear mass density of fibres. In other words, a low dtex value corresponds to a thin fibre.

In embodiments of the present invention, the fibre has a dtex of below 50, such as below 20 such as below 10.

In embodiments of the present invention, the polymer fibre has a thickness below 0.2 mm, such as below 0.1 mm.

In embodiments of the invention, the total number average molecular weight of the thermoplastic polymer is between 10,000 and 1,000,000 g/mol As an example, the total number average molecular weight of the thermoplastic polymer is at least 10,000 g/mol, but preferably not more than 1,000,000 g/mol. The molecular weight may be 15,000 g/mol or more, or 50,000 g/mol or more, or 100,000 g/mol or more, or less than 1,000,000 g/mol, or less than 500,000 g/mol.

In embodiments of the invention, the fibre has a free swell absorbency of at least 10 gram Solution A per gram of fibre, as measured by the free swell method.

As discussed above, the polymer fibre may be obtained by melt spinning and/or by various non-woven melt processes, inter alia meltblowing and/or spunlaying, and the polymer fibre has an absorbency of at least 10 gram Solution A per gram of fibre, as measured by the free swell method, or, in another embodiment, of at least 15 gram Solution A per gram of fibre. Further, the polymer fibres as per the present invention may have free swell absorbency values of at least 20 gram Solution A per gram of fibre, or of at least 30 gram Solution A per gram of fibre, or a free swell absorbency in a range made up of any combination of the above-mentioned values, or any combination of the above-mentioned values and any other values suitable for the purposes of the present invention.

As an example, the polymer fibre may have an absorbency of at least 15 gram Solution A per gram of fibre, as measured by the free swell method.

The free swell method to determine the capacity of the fibre to absorb and retain polar liquids may be performed according to the following procedure: Solution A was used as the model liquid. Solution A is made up by weighing in 8.298 g NaCl and 0.368 g $CaCl_2$ in a 1 liter metering flask and then filling up with distilled water to create a solution having a volume of about 1 liter. All tests were performed in a conditioned room with a temperature of 23° C.±2 and a relative humidity of 50%±2.

The free swell method may be carried out as follows:

1) Weigh in 0.5 g fibres in a 100 ml beaker. Weigh in 30 g Solution A and quickly poor the Solution A over the fibres and shake it carefully for 5 seconds to get a good distribution.

2) Let the fibres swell in Solution A for 5 minutes (±10 s).

3) Filter out excess liquid using a Buchner funnel Ø 70 mm, with a Quantitative filter paper Grade 00R Ø 70 mm in it. Saturate the filter paper by pouring 10 ml of Solution A through the funnel. When it stops dripping, or when it is ≥5 seconds between the drops, shake the funnel carefully.

4) Put a weighed beaker, W1, under the funnel. Pour the fibre solution/gel (i.e. the fibres dispersed in Solution A) in the funnel and let it filtrate for 10 minutes (±10 s).

5) Shake the funnel carefully. Weigh the beaker, W1, containing the filtered Solution A again, to get the value W2. The free swell absorbency (expressed in grams of Solution A absorbed per gram of fibre) is calculated according to the following formula:

$$2 \times (30-(W2-W1)) = FSA = \text{grams absorbed Solution A/gram fibre}$$

In embodiments of the invention, the fibre may have a retention capacity of at least 5 g/g The retention capacity of a fibre may be determined directly after the free swell absorbency has been measured. The absorbing fibres are, when fully absorbed according to the free swell method as described above, subjected to a static pressure of 20 mm Hg. The retention capacity is defined as the difference between the amount of absorbed liquid and the amount of liquid squeezed out. To determine the retention of the fibres the following procedure was used:

1) Put a weighed beaker, W3, under the funnel.

2) Put a Ø 70 mm plate onto the test material in the funnel and weights on top. The total weight shall create a pressure of 20 mmHg (including the weight of the plate in the calculation). Let the pressure remain for 5 minutes (±10 s). Shake the funnel carefully.

3) Weigh the beaker with the excess test liquid again, to obtain the value W4.

The retention capacity is calculated as grams of liquid left in the test piece after added pressure per g of dry fibre and as the difference between the amount of absorbed liquid and the amount of liquid squeezed out, as follows:

$$(FSA - 2 \times (W4-W3)) = R = \text{liquid left in the test piece after an added pressure of 20 mmHg/g fibre}$$

The fibre of the present invention may have a tenacity of at least 10 cN/tex.

Thus, In accordance with a further embodiment of the present invention, the polymer fibres of the present invention may have a tenacity of at least 10 cN/tex, and preferably at least 15 cN/tex. The tenacity in cN/tex is calculated from the breaking force and the linear density, according to the following formula:

$$\text{Tenacity}(cN/tex) = (\text{Breaking Force}[N])/(\text{linear density}[dtex] \times 0.001)$$

The skilled person is well aware of how to obtain the values of breaking force and linear density and thereby also how to calculate the tenacity of the polymer fibres. Further as per the present invention, the polymer fibre may have a tenacity of at least 20 cN/tex, or at least 30 cN/tex, or a tenacity in a range made up of any combination of the above-mentioned values, or any combination of the above-mentioned values and any other values suitable for the purposes of the present invention.

In yet another embodiment in accordance with the present invention, the polymer fibres may have a retention capacity value of at least 10 g Solution A per gram of fibre, as measured by the above outlined method for determining the retention capacity. Further as per the present invention, the retention capacity of the polymer fibres may be at least 15 g Solution A per gram of fibre, or preferably at least 20 g Solution A per gram of fibre. Further, the polymer fibres as per the present invention may have retention capacity values of at least 30 gram Solution A per gram of fibre, or a retention capacity in a range made up of any combination of the above-mentioned values, or any combination of the above-mentioned values and any other values suitable for the purposes of the present invention.

In embodiments, the polymer fibre comprises at least one substance internally and/or externally.

In accordance with another embodiment, the polymer fibre may comprise for instance at least one added substance, either internally and/or externally, in order to improve the properties of the fibre and/or to provide additional properties. By internal addition is meant that the substance is mixed in the polymer prior to fibre-making. This can be combined with for instance core sheath fibres where the substance can be present in different concentrations in the core and sheath. Different substances can be present in the core and sheath. By external addition is meant that the substance is added to the already made fibre and/or nonwoven by spraying or dipping, etc. Internal and external addition of substances can be combined. In a further embodiment, the at least one substance that may be present internally and/or externally may be, inter alia, an antimicrobial agent selected from a group comprising silver, silver salts, zinc, zinc salts, iodine, iodine complexes, chlorhexidine, cationic substances such as poly hexamethyl biguanide and/or polyquaternium polymers, and/or any mixtures or combinations thereof. Further, the at least one substance that may be present internally and/or externally may be selected from the group comprising vitamins, peptides, growth factors, nucleic acids and/or mixtures or combinations thereof.

The location, internal or external, of the additional at least one substance depends on numerous parameters, such as the release time point, the purpose of the substance(s), and the polymer components. If the substances are to be released, for example, relatively late during the use of a wound dressing, it may be suitable to position the substance(s) internally. However, if the substance(s) are to be utilized initially when for example a wound dressing is used, the substance(s) could be applied externally. Further, the positioning also depends on the release properties of the polymer and the polymer fibre, as well as characteristics relating to the active substance(s) per se, for instance in terms of heat and shear stability.

As an example, the at least one substance internally and/or externally may be selected from an antimicrobial agent selected from a group comprising silver, silver salts, zinc, zinc salts, iodine, iodine complexes, poly hexamethyl biguanide, chlorhexidine and/or any mixtures or combinations thereof; and/or any of the following: vitamins, peptides, growth factors, nucleic acids and/or mixtures or combinations thereof.

In embodiments of the invention, the thermoplastic polymer comprises additives for improved runability, spreading of liquids, luster, feel, etc., added internally and/or externally.

In line with a further embodiment, the polymer fibre may comprise additives for improved runability, spreading of liquids, luster, feel, etc., added internally and/or externally. In yet another embodiment, the additives may be selected from the group comprising paraffin waxes, silicone oils, esters, stearates, and tensides.

In embodiments of the first or second aspect, there is provided a multi-component polymer fibre comprising a polymer fibre according to the first or second aspect and at least one additional thermoplastic polymer.

The present invention additionally pertains to multi-component polymer fibres, wherein polymer is spun together with other thermoplastic polymers to form core-sheath, island-in-a-sea, side-by-side, or other types of fibres wherein two or more polymers are combined.

It may be an advantage to combine the copolymer in the fibre with some other material having different properties. The fibres may for example be able to curl when two different polymers are used in a fibre if the polymers have different crimp properties, resulting in the formation of curled fibres. A core-sheath fibre can be prepared having for instance a reinforcing core covered with a gelling sheath. The technology to combine two or more melt processable polymers in a fibre may also be used to control release of active substances, with for instance different swelling speed of the different polymers.

As an example, the multi-component fibre may be obtained by spinning the thermoplastic polymer together with the at least one additional thermoplastic polymer to form core-sheath, island-in-a-sea, side-by-side, or other types of fibres wherein two or more polymers are combined.

The thermoplastic polymer used in the present invention can be used in combination with other polymers to form core-sheath, island-in-a-sea or side-by-side polymer fibres. Non-woven and/or woven fabrics can also be made by combining fibres of other materials with fibres made from the polymer in the present invention in order to improve special features. Further, the fibres can be given different shapes and/or structure by curling the fibre.

As a third aspect of the invention, there is provided a method for providing a polymer fibre, comprising
a) providing a thermoplastic polymer comprising
hexamethyl diisocyanate (HDI) reacted with
at least one polyol, and
at least one chain extender
wherein the at least one chain extender comprises a diol and wherein the molar ratio of polyol to chain extender is from 20:80 to 65:35;
b) melting the thermoplastic polymer; and
c) preparing polymer fibres from the melted polymer obtained in step b).

The third aspect is based on the insight that that thin fibres may be prepared from a thermoplastic polymer comprising hexamethyl diisocyanate (HDI) reacted with at least one polyol, and at least one chain extender wherein the at least one chain extender comprises a diol and wherein the molar ratio of polyol to chain extender is from 20:80 to 65:35. This is due to the high melting point of such thermoplastic polymers. Further, a fibre prepared by the method of the third aspect also has a high absorption capacity, as seen in the Experimental Examples below.

Consequently, the third aspect of the invention relates to a process for the preparation of polymer fibres, comprising, inter alia, the steps of providing a suitable polymer, melting it, and subsequently preparing polymer fibres from the melted polymer. The first prerequisite for fibre spinning is having the right polymer rheology, but it is also important that the polymer melt does not contain too much gels. Gel spots in the melt can be caused by cross linked (physically or chemically) regions or regions with higher molecular weight polymer. If the polymer has the right rheology for fibre spinning successful fibre spinning can be achieved by optimizing the process parameters in the fibre spinning process. Temperature, residence time/speed on the extruder, and pressure are important parameters to get good and even melt without getting to much degradation of the polymer. If the residence time is too low there is a risk that the polymer is not completely melted and if the residence time is too long there is a risk that the polymer degrades. A degraded polymer leads to a lower viscosity of the melt and it also leads to weaker fibres and ultimately to less good gel properties. The residence time, the speed of the extruder and the pressure are interrelated. Higher speed of the extruder leads to shorter residence time and higher pressure. The pressure in the extruder is not only determined by the extruder speed but is also affected by the spinneret design. The spinneret design can be varied by using different hole sizes, hole shapes and by the number of holes per surface square. The length divided by the hole diameter (D) is an important measure for spinnerets. The length (L) is defined as the distance from the orifice to the point where the distance between the walls of the hole starts to increase (FIG. 1). A standard value for length divided by the hole diameter is two but generally a higher value leads to better spinnability but also higher pressure in the extruder for similar hole size and number of holes per surface square.

The thermoplastic polymer in the method of the third aspect of the invention may be as discussed in relation to the first aspect above. Thus, the thermoplastic polymer may comprise the following building blocks A and B:

$$—O—(CH_2—CH_2—O)_n— \quad (A)$$

$$—O—[CH_2]_y—O— \quad (B)$$

n indicating a repeating unit and being an integer of 10-400, and
y being an integer in the range of 2 to 16,
wherein:
A is present in an amount of 15-30 mole %, B is present in an amount of 20-40 mole %, wherein building blocks A and B are linked by the following linking group C:

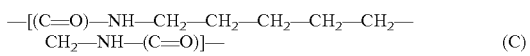 (C)

wherein

C is present in an amount of 45-55 mole %

In embodiments of the third aspect, step a) comprises reacting a group of components comprising hexamethyl diisocyanate (HDI)

at least one polyol, and at least one chain extender wherein the at least one chain extender comprises a diol and wherein the molar ratio of polyol to chain extender is from 20:80 to 65:35.

Thus, the thermoplastic polymer may be as described in relation to the second aspect above.

Further, in embodiments of the third aspect, step (c) is carried out by melt spinning or by processing the polymer in non-woven melt processes In other words, the polymer fibres of the present disclosure may be prepared from the melted polymer using for instance melt spinning and/or by processing the polymer in non-woven melt processes, for instance meltblowing or spunlaying.

There are essentially three main classes of fibre spinning technologies: Dry spinning, wet spinning, and melt spinning. Melt spinning is the preferred method from a production standpoint, since no drying or removal of solvents is needed. In dry spinning the polymer is dissolved in a solvent and the solution is spun through a spinneret. The solvent is removed from the fibre as soon as the fibre is formed. In wet spinning the polymer is dissolved in a solvent and the solution is spun through a spinneret into a coagulating bath where the fibre is formed.

Fibres made from any of the mentioned spinning technologies can be used for making non-woven or woven fabrics, but only thermoplastic polymers can be used in meltblown or spunlaid processes since the melt spinning and nonwoven making is made in one step. Other nonwoven making methods that can be used for these kinds of fibres are drylaid with carding or airlaying. The web bonding, i.e. the bonding of the fibres in the nonwoven, is carried out chemically, thermally, or mechanically. The different methods for making web formation and web bonding give different features to the nonwoven. For a non-woven suitable for use in open wounds a preferred nonwoven is made using the drylaid method, with carding and mechanical web bonding with needle punching. However, the method depends on the intended use of the nonwoven or woven fabric.

In one embodiment, the polymer provided for the process is a polyurethane polymer comprising PEG. The polymer is melted and polymer fibres are finally prepared from the melted polymer. In another embodiment, the polyurethane polymer utilized in the process may comprise between approximately 70-95 weight %, preferably between approximately 81-94 weight %, and most preferably between approximately 84-93 weight % PEG.

In accordance with further embodiments as per the present invention, the temperature of the melt is between approximately 150° C. and approximately 200° C., and the residence time in the extruder may be ranging from approximately 5 minutes to approximately 20 minutes, preferably 10 minutes. In one embodiment, the melted polymer may be extruded through a 0.5 mm orifice, and, in yet another embodiment, the polymer may be stretched to a diameter ranging from approximately 5 micron to approximately 20 micron, preferably 10 micron. The size of the orifice may vary from approximately 0.15 mm to 0.6 mm in commercial spinnerets.

As a fourth aspect of the invention, there is provided an absorbent article, such as a wound dressing, an ostomy device, a diaper, a sanitary napkin, a panty liner or the like, characterized in that the article comprises the fibre according to the first or second aspect above As an example, the absorbent article may be a wound dressing.

Thus, an additional aspect of the present invention pertains to absorbent articles, such as for instance wound dressings, ostomy devices, diapers, sanitary napkins, panty liners or the like, wherein the articles comprise polymer fibres in accordance with the present invention. As per one embodiment, the absorbent article is for instance a wound dressing, or any other type of dressing intended for use in treating and/or protecting a wound, an injury, and/or a burn.

In a further embodiment, the polymer fibres comprised in the absorbent articles comprises inter alia polyurethane polymers comprising PEG.

As a fifth aspect of the invention, there is provided the use of the fibre according to the first or second aspect in a product for treating wounds and/or burns.

Consequently, yet another aspect of the present invention relates to the use of the polymer fibres as per the present invention, for instance in products for treating and/or protecting wounds and/or burns. In one embodiment, the polymer fibres used in the products for treating wounds and/or burns comprise polyurethane polymers comprising PEG.

EXPERIMENTAL EXAMPLES

The polymers have been synthesized with the intention of producing polymers with a low amount of branching and cross linking, with the molecular weight ranging from about $1 \times 10^4$ to about $1 \times 10^6$ g/mol (i.e. 10 kDa to 1 MDa). The properties of the thermoplastic polymer and also the obtained fibre from the thermoplastic polymer may be influenced by the choice and amount of catalyst and stabilizers and various process parameters. The polymer can be made in any type of conventional synthesis routes, such as running the synthesis in a solvent, as a batch process, or as a continuous process, for instance reactive extrusion. The best process parameters as well as the catalyst type and amount and stabilizer have to be adopted for each and every type of polymer and process.

The diisocyanates was supplied by Bayer Material Science AG, Leverkusen, Germany. Borchi Kat 24 was supplied by Borchers GmbH, Germany. All other chemicals was supplied by Sigma-Aldrich and used without further purification.

The following example polymers (1-9) was prepared:

Example Polymer 1

A mixture of 547 g PEG 8000 and 34.7 g PEG 2000 was dried in a vessel under vacuum (approx. 20 mbar) for 2 hours at 100° C. The mixture was stirred under nitrogen and 0.34 g of dibutylphosphate and 9.6 g of 1,12-dodecanediol were added. After heating to 120° C., 34.9 g Methylene bis(4-cyclohexylisocyanate) and 0.34 g tin-II-ethylhexanoate were added and the vessel was heated until the final temperature of 196° C. was reached (approx 20 min). The resulting polymer was poured to a tray and stored at 105° C. for 1 hour.

The maximum draw ratio was 6.2 for this polymer and the free swell absorbency and retention values were 28.8 g/g and 25.1 g/g, respectively. The formed gel was strong and clear.

Example Polymer 2

A mixture of 530.5 g PEG 8000 and 33.6 g PEG 2000 was dried in a vessel under vacuum (approx. 20 mbar) for 2 hours at 100° C. The mixture was stirred under nitrogen and 0.66 g of dibutylphosphate and 6.27 g of 1,4-butandiol were added. After heating to 120° C., 41.1 g Methylene bis(4-cyclohexylisocyanate) and 0.33 g Borchikat 24 were added and the vessel was heated until the final temperature of 196° C. was reached (approx 15 min). The resulting polymer was poured to a tray and stored at 105° C. for 1 hour.

The fibre spinning properties was evaluated according to the standard test described above and the maximum draw ratio was 6.2. The free swell absorbency and retention values were 29.0 g/g and 25.9 g/g, respectively. The formed gel was completely clear and strong.

Example Polymer 3

A mixture of 526.1 g PEG 8000, 33.4 g PEG 2000 and 16.74 g of Hydroquinone bis(2-hydroxyethyl)ether was dried in a vessel under vacuum (approx. 20 mbar) for 2 hours at 100° C. The mixture was stirred under nitrogen and 0.30 g of dibutylphosphate was added. After heating to 110° C., 0.30 g tin-II-ethylhexanoate and 26.9 g 1,6-Hexamethylendiisocyanat were added and the vessel was heated until the final temperature of 180° C. was reached (approx 5 min). The resulting polymer was poured to a tray and stored at 105° C. for 1 hour.

To evaluate the fibre spinning and fibre properties Polymer 1 was run in the lab set up for fibre spinning. The highest draw ratio that was possible to achieve was 6.2 and the free swell absorbency and retention were 25.2 g/g and 17.38 g/g, respectively. The formed gel was creamy with some fibre structure.

Example Polymer 4

A mixture of 549.7 g PEG 8000 and 34.8 g PEG 2000 was dried in a vessel under vacuum (approx. 20 mbar) for 2 hours at 100° C. The mixture was stirred under nitrogen and 1.88 g of dibutylphosphate and 6.5 g of 1,4-Butandiol were added. After heating to 165° C., 38.08 g 4,4-Diphenylmethandiisocyanat were added and the vessel was heated until the final temperature of 196° C. was reached (approx 5 min). The resulting polymer was poured to a tray and stored at 105° C. for 1 hour.

The maximum draw ratio of this polymer was 12.4 and the free swell and retention was 24.8 g/g and 16.8 g/g, respectively. The gel was strong and clear.

Example Polymer 5

575.4 g of PEG 8000 as dried in a vessel under vacuum (approx. 20 mbar) for 2 hours at 100° C. The mixture was stirred under nitrogen and 0.30 g of dibutylphosphate and 12.4 g of 1,4-butandiol and 0.30 g tin-II-ethylhexanoate were added. After heating to 110° C., 35.1 g 1,6-Hexamethylendiisocyanat were added and the vessel was heated until the final temperature of 160° C. was reached (approx 6 min). The resulting polymer was poured to a tray and stored at 105° C. for 1 hour.

Example Polymer 6

528.0 g of PEG 2000 was dried in a vessel under vacuum (approx. 20 mbar) for 2 hours at 100° C. The mixture was stirred under nitrogen and 0.38 g of dibutylphosphate and 24.1 g of 1,4-butandiol and 0.38 g tin-II-ethylhexanoate were added. After heating to 110° C., 87.0 g 1,6-Hexamethylendiisocyanat were added and the vessel was heated until the final temperature of 160° C. was reached (approx 3 min). The resulting polymer was poured to a tray and stored at 105° C. for 1 hour.

Example Polymer 7

583.5 g of PEG 2000 was dried in a vessel under vacuum (approx. 20 mbar) for 2 hours at 100° C. The mixture was stirred under nitrogen and 0.30 g of dibutylphosphate and 11.4 g of 1,4-butandiol and 0.30 g tin-II-ethylhexanoate were added. After heating to 110° C., 68.7 g 1,6-Hexamethylendiisocyanat were added and the vessel was heated until the final temperature of 160° C. was reached (approx 2 min). The resulting polymer was poured to a tray and stored at 105° C. for 1 hour.

Example Polymer 8

553.8 g of PEG 4000 was dried in a vessel under vacuum (approx. 20 mbar) for 2 hours at 100° C. The mixture was stirred under nitrogen and 0.30 g of dibutylphosphate and 12.7 g of 1,4-butandiol and 0.30 g tin-II-ethylhexanoate were added. After heating to 110° C., 45.8 g 1,6-Hexamethylendiisocyanat were added and the vessel was heated until the final temperature of 160° C. was reached (approx 4 min). The resulting polymer was poured to a tray and stored at 105° C. for 1 hour. The maximum draw ratio was 15.1 and the free swell and retention values were 17.7 g/g and 10.7 g/g, respectively. The gel was made up of swelled fibres.

Example Polymer 9

A mixture of 537.3 g of PEG 8000 and 44.7 g PEG 1000 was dried in a vessel under vacuum (approx. 20 mbar) for 2 hours at 100° C. The mixture was stirred under nitrogen and 0.30 g of dibutylphosphate and 15.2 g of 1,4-butandiol and 0.30 g tin-II-ethylhexanoate were added. After heating to 110° C., 45.8 g 1,6-Hexamethylendiisocyanat were added and the vessel was heated until the final temperature of 160° C. was reached (approx 4 min). The resulting polymer was poured to a tray and stored at 105° C. for 1 hour.

The spinnability was good for this polymer and the maximum draw ratio was 30.5 and the free swell and retention values were 23.3 g/g and 15.7 g/g, respectively. The gel was clear and strong with some fibre structure.

Results

The results are summarized in Table 1 below, in which the column A-R denotes the following A=Experimental polymer number
B=The molar ratio of the PEG to the chain extender
C=The type of chain extender
D=The number average molecular weight of the PEG E=The type of diisocyanate. HMDI=methylene bis(p-cyclohexyl isocyanate; HDI=hexamethyl diisocyanate; MDI=methylene bis (p-phenyl isocyanate.
F=Melting point of the fibre
G=Free swell absorbancy of fibre
H=Retention capacity of fibre
I=Weight % of PEG
J=Weight % of diisocyanate
K=Weight % of chain extender
L=Mole % of PEG
M=Mole % of diisocyanate
N=Mole % of chain extender
O=Polyurethane density of fibre expressed as mole isocyanate/kg
P=Mass in grams per 10,000 meters (dtex) of fibre
Q=Draw ratio of fibre
R=Ratio of high molecular PEG to low molecular PEG As seen in Table 1, Example polymers 5, 6, 8 and 9 fall under the scope of the present invention, whereas example polymers 1, 2, 3, 4, 7 represent polymer fibres that do not form part of the present invention. Thus, a skilled person understand that Example polymers 5, 6, 8 and 9 represent a polymer fibre comprising a thermoplastic polymer comprising the following building blocks A and B:

$$—O—(CH_2—CH_2—O)_n—$$ (A)

$$—O—[CH_2]_y—O—$$ (B)

n indicating a repeating unit and being an integer of 10-400, and
y being an integer in the range of 2 to 16,
wherein:
A is present in an amount of 15-30 mole %,
B is present in an amount of 20-40 mole %,
wherein building blocks A and B are linked by the following linking group C:

$$—[(C=O)—NH—CH_2—CH_2—CH_2—CH_2—CH_2—CH_2—NH—(C=O)]—$$ (C)

wherein
C is present in an amount of 45-55 mole %.

In other words, Example polymers 5, 6, 8 and 9 has been prepared by reacting different PEGs (forming building block A of the prepared polymer) with a diol as chain extender (forming building block B of the prepared polymer) and HDI (forming linking group C of the prepared polymer).

Thus, it is evident that polymer fibres of the present invention have a superior melting point of above 100° C. as compared to the other polymers. For example, the inventors have found that diisocyanate compounds other than HDI do not give the fibre a high melting point. Further, Table 1 shows that HQEE (which is not a diol) as chain extender together with HDI (Example 3) does not give the fibre a high melting point.

Thus, the results clearly shows that HDI in combination with a diol gives the prepared polymer a high melting point together with low dtex values, i.e. very thin fibres.

Further, Example 7 as compared to Example 6 and 8, shows that the amount of PEG is important. To high amount of PEG, as in Example 7 (PEG=35 mole %), do not give the polymer a high melting point. This indicates that the number or density of hard segments (comprising HDI and chain extender) is important for obtaining a fibre of high melting point.

Furthermore, Example 9 shows that the combination of a PEG of low molecular weight (1000) and high molecular weight (8000) further gives the polymer a high free swell absorbancy, i.e. a high capacity of absorbing liquid, in combination with the capacity of forming a very thin fibre from the polymer (a dtex as low as 3).

TABLE 1

Results from the preparation of fibres

| A Ex. | B PEG:Chain extender | C Chain extender | D PEG | E Diisocyanate | F Melting point fiber | G Free swell g/g Sol A | H Ret. g/g Sol A | I PEG weight % | J Diisocyanate weight % |
|---|---|---|---|---|---|---|---|---|---|
| 1 | 65.35 | 1,12-dodecanediol | 8000 2000 | HMDI | 65 | 28.8 | 25.1 | 92.9 | 5.6 |
| 2 | 55:45 | 1,4-Butanediol | 8000, 2000 | HMDI | 55 | 29.0 | 25.9 | 92.3 | 6.7 |
| 3 | 50:50 | HQEE | 8000, 2000 | HDI | 60 | 25.2 | 17.4 | 92.8 | 4.5 |
| 4 | 55:45 | 1,4-Butanediol | 8000, 2000 | MDI | 55 | 24.8 | 16.8 | 92.9 | 6.1 |
| 5 | 35:65 | 1,4-Butanediol | 8000 | HDI | 115 | | | 92.4 | 5.6 |
| 6 | 50.50 | 1,4-Butanediol | 2000 | HDI | 100 | 9.9 | 5.4 | 82.6 | 13.6 |
| 7 | 70:30 | 1,4-Butanediol | 2000 | HDI | 60 | 5.5 | 4.8 | 87.9 | 10.4 |
| 8 | 50:50 | 1,4-Butanediol | 4000 | HDI | 115 | 17.7 | 10.7 | 90.4 | 7.5 |
| 9 | 40:60 | 1,4-Butanediol | 8000, 1000 | HDI | 110 | 23.3 | 15.7 | 90.5 | 7.1 |

| A Ex. | K Chain-extender weight % | L PEG mole % | M Diisocyanate mole % | N Chain-extender mole % | O Polyur. density mole isocy/kg | P dtex | Q Draw ratio | R High Mn PEG:Low Mn PEG |
|---|---|---|---|---|---|---|---|---|
| 1 | 1.5 | 32.2 | 50.0 | 17.8 | 0.44 | 61 | 6 | |
| 2 | 1.0 | 26.9 | 50.6 | 22.5 | 0.51 | 61 | 6 | 80:20 |
| 3 | 2.8 | 25.2 | 48.9 | 25.8 | 0.53 | 61 | 6 | 80:20 |
| 4 | 1.0 | 27.7 | 49.0 | 23.2 | 0.48 | 15 | 12 | 80:20 |
| 5 | 2.0 | 17.2 | 49.9 | 32.9 | 0.67 | 49 | 7 | 100:0 |
| 6 | 3.8 | 25.2 | 49.3 | 25.5 | 1.62 | 7 | 18 | 100:0 |
| 7 | 1.7 | 35.3 | 49.4 | 15.3 | 1.23 | 8 | 17 | 100:0 |
| 8 | 2.1 | 25.1 | 49.4 | 25.5 | 0.89 | 10 | 15 | 100:0 |
| 9 | 2.4 | 20.2 | 49.3 | 30.5 | 0.85 | 3 | 31 | 60:40 |

The invention claimed is:

1. An absorbent article comprising a polymer fibre comprising a thermoplastic polymer consisting of building blocks A and B and linking group C:

—O—(CH₂—CH₂—O)ₙ— (A)

—O—[CH₂]ᵧ—O— (B)

wherein:
n is an integer of 10-400, and
y is an integer of 4 to 16
wherein:
A is present in an amount of 15-30 mole %,
B is present in an amount of 20-40 mole %,
wherein building blocks A and B are linked by the following linking group C:

—[(C=O)—NH—CH₂—CH₂—CH₂—CH₂—CH₂—CH₂—NH—(C=O)]— (C)

wherein:
C is present in an amount of 45-55 mole %,
wherein the thermoplastic polymer has a melting point of at least 100° C.,
wherein the polymer fibre is in fibre form at 70° C., and
wherein the absorbent article is a wound dressing.

2. The absorbent article according to claim 1, wherein linking group C originates from hexamethyl diisocyanate (HDI).

3. The absorbent article according to claim 1, wherein building block A originates from polyethylene glycol (PEG).

4. The absorbent article according to claim 3, wherein the number average molecular weight of said PEG is between 400-16000 g/mole.

5. The absorbent article according to claim 3, wherein A originates from a first PEG and a second PEG, wherein the number average molecular weight of the first PEG is different than the number average molecular weight of the second PEG.

6. The absorbent article according to claim 5, wherein the molar ratio between the first PEG and the second PEG is from 1:1 to 1:10.

7. The absorbent article according to claim 5, wherein the first PEG has a number average molecular weight of 400 to 3,000 g/mole and the second PEG has a number average molecular weight of 6,000 to 16,000 g/mole.

8. The absorbent article according to claim 7, wherein the molecular weight of the first PEG is from 1,000 to 2,000 g/mole and the molecular weight of the second PEG is from 6,000 to 9,000 g/mole.

9. The absorbent article according to claim 1, wherein the thermoplastic polymer is substantially linear.

10. The absorbent article according to claim 1, wherein the thermoplastic polymer comprises soft and hard segments and wherein said hard segments comprises B and C building blocks and said soft segments comprises A building blocks.

11. The absorbent article according to claim 1, wherein B originates from at least one diol.

12. The absorbent article according to claim 11, wherein said at least one diol is selected from the group consisting of 1,4 butanediol, 1,6-hexanediol, 1,8-octanediol, 1,10-decanediol, 1,12-dodecanediol, cyclododecanediol, 1,14-tetradecanediol, and 1,16-hexadecanediol.

13. The absorbent article according to claim 12, wherein the at least one diol is 1,4 butanediol.

14. The absorbent article according to claim 1, wherein the polymer fibre has a thickness below 0.2 mm.

15. The absorbent article according to claim 1, wherein the fibre absorbs at least 10 gram of a solution comprising 8.298 g/L NaCl and 0.368 g/L CaCl₂ per gram of fibre.

16. The absorbent article according to claim 1, wherein the fibre has a tenacity of at least 10 cN/tex.

17. The absorbent article according to claim 1, wherein the polymer fibre comprises at least one substance internally and/or externally.

18. The absorbent article according to claim 17, wherein said at least one substance internally and/or externally is selected from an antimicrobial agent selected from the group consisting of silver, silver salts, zinc, zinc salts, iodine, iodine complexes, poly hexamethyl biguanide, and chlorhexidine and/or any mixtures or combinations thereof; and/or any of the following: vitamins, peptides, growth factors, and nucleic acids and/or mixtures or combinations thereof.

19. The absorbent article according to claim 1, wherein the thermoplastic polymer comprises additives for improved runability, spreading of liquids, luster, or feel, added internally and/or externally.

20. The absorbent article according to claim 1, wherein the polymer fibre comprises at least one additional thermoplastic polymer.

21. The absorbent article according to claim 20, wherein the polymer fibre is obtained by spinning said thermoplastic polymer together with said at least one additional thermoplastic polymer to form core-sheath, island-in-a-sea, or side-by-side wherein two or more polymers are combined.

22. The absorbent article according to claim 1, wherein the polymer fibre has a dtex value of less than 20.

23. A method for providing the absorbent article of claim 1, comprising
a) providing the thermoplastic polymer of claim 1, wherein the molar ratio of building block (A) to building block (B) is from 20:80 to 65:35;
b) melting said thermoplastic polymer; and
c) preparing the polymer fibre from the melted polymer obtained in step b).

24. A method according to claim 23, wherein step (c) is carried out by melt spinning or by processing the polymer in non-woven melt processes.

* * * * *